United States Patent

Pomeranz et al.

[11] Patent Number: 5,993,462
[45] Date of Patent: Nov. 30, 1999

[54] SHAPABLE CATHETER USING EXCHANGEABLE CORE AND METHOD OF USE

[75] Inventors: Mark L. Pomeranz, Los Gatos; Darren R. Sherman, Los Altos, both of Calif.; Troy J. Chapman, East Avilla, Ind.; Peter Park, Santa Clara, Calif.

[73] Assignee: Cardiac Pathways Corporation, Sunnyvale, Calif.

[21] Appl. No.: 09/049,342

[22] Filed: Mar. 27, 1998

Related U.S. Application Data

[63] Continuation-in-part of application No. 08/680,426, Jul. 15, 1996.

[51] Int. Cl.[6] .......................................................... A61B 5/04
[52] U.S. Cl. .............................. 606/129; 604/281; 606/45; 606/108; 600/508
[58] Field of Search .............................. 604/95, 280, 282, 604/281; 606/1, 110, 113, 129, 159, 167, 170, 108, 45–52, 32; 600/508

[56] References Cited

U.S. PATENT DOCUMENTS 5,843,091  12/1998  Holsinger et al. ....................... 606/108
5,865,800   2/1999  Mirarchi et al. ........................... 604/95

Primary Examiner—Glenn K. Dawson
Attorney, Agent, or Firm—Limbach & Limbach

[57] ABSTRACT

In a shapable catheter and method for positioning a shapable catheter within a body cavity, a core wire is provided which includes a pre-shaped region bent into a predetermined shape. A catheter is provided which includes a lumen proportioned to slidably receive the core wire. The catheter includes a rigid proximal section and a flexible distal section. A pull wire may additionally be provided to allow the user to cause deflection at a distal portion of the catheter.

35 Claims, 14 Drawing Sheets

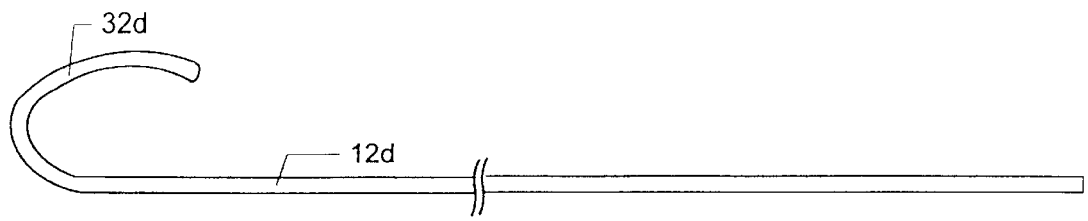
FIG. 3B
FIG. 4
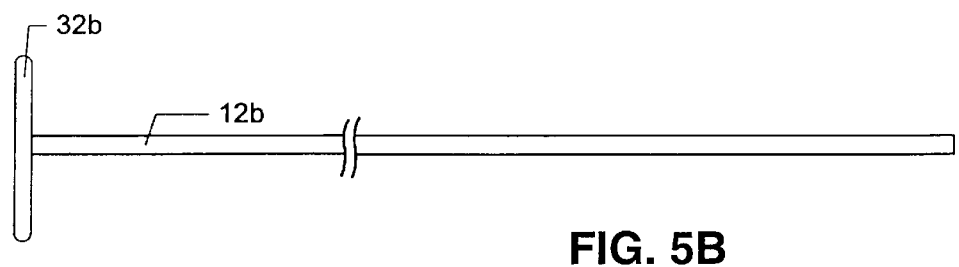
FIG. 5B
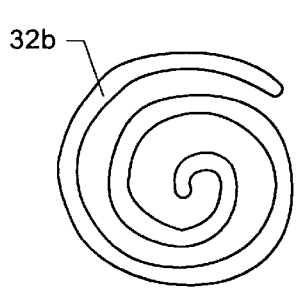 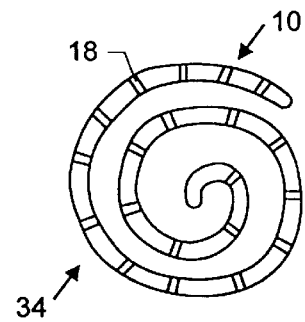
FIG. 5A  FIG. 5C

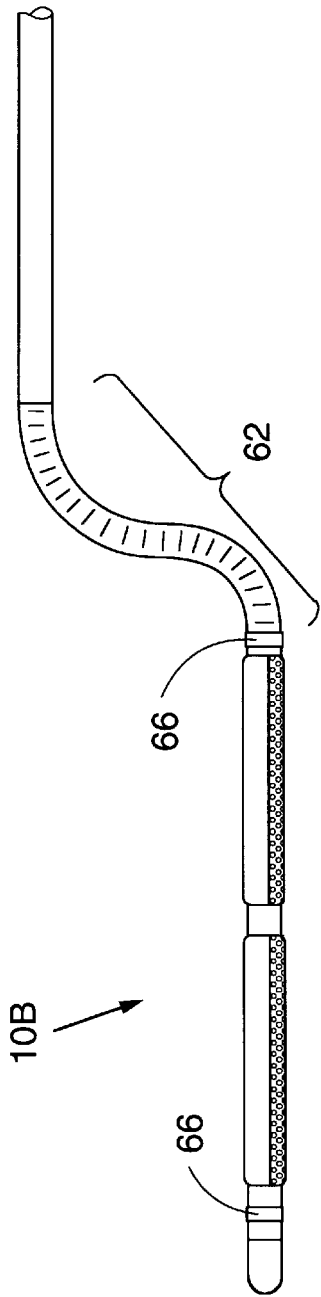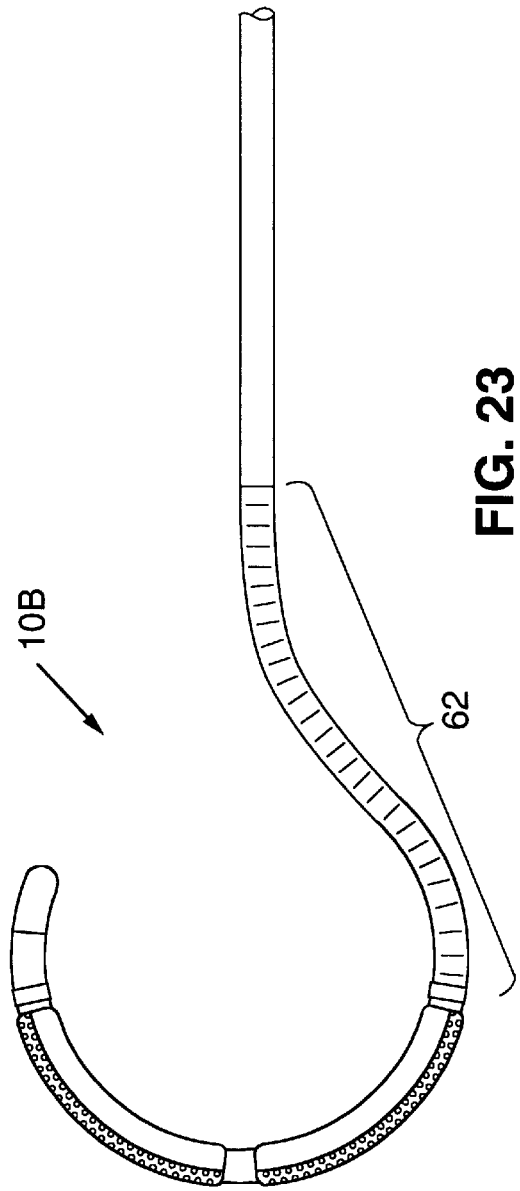

SHAPABLE CATHETER USING EXCHANGEABLE CORE AND METHOD OF USE

This is a continuation-in-part of application Ser. No. 08/680,426, filed Jul. 15, 1996.

FIELD OF THE INVENTION

The present invention relates generally to the field of medical catheters. In particular, the present invention relates to the field of catheters of the type used for mapping electrical activity within the heart and for ablating cardiac tissue.

BACKGROUND OF THE INVENTION

There are a number of conditions in the heart which necessitate monitoring the cardiac tissue for sources of abnormal electrical activity within the heart and/or which require ablation of tissue within the heart where such sources of electrical activity are located.

Two such conditions are atrial fibrillation and ventricular tachycardia. Atrial fibrillation is a condition in the heart in which abnormal electrical signals are generated in the endocardial tissue to cause irregular beating of the heart. One method used to treat atrial fibrillation involves creating several long (i.e. approximately 2–10 cm) lesions on the endocardium within the atria. These lesions are intended to stop the irregular beating of the heart by creating barriers between regions of the atria. These barriers halt the passage through the heart of the abnormal currents generated by the endocardium. This procedure is commonly referred to as the "maze procedure" because it creates a maze of lesions design to block the passage of abnormal currents through the heart.

Existing procedures for forming such linear lesions include the highly invasive technique of opening the patient's chest and heart and forming linear incisions inside the atria. Naturally, the highly invasive nature of this procedure makes it a particularly high risk to the patient and necessitates extraordinarily long recovery time.

Other attempts have been made to form the linear lesions using ablation catheters fed into the heart via the patient's vessels (i.e., the arteries or veins). For example, one such procedure involves inserting into the atria a 7 French catheter having an ablation tip. Radio frequency (RF) energy is supplied to the tip as the tip is dragged across the endocardium, thereby burning linear lesions into the endocardium.

While often successful for forming linear lesions, the ablation tip of the catheter can sometimes lift off of the surface of the endocardium as it is dragged across the endocardium, creating one or more breaks in the lesion. Such breaks minimize the success of the ablation procedure by leaving a path through which current may travel during atrial fibrillation episodes.

Ventricular tachycardia is another condition which generates abnormal electrical activity in the heart and which can require ablation of cardiac tissue associated with the abnormal electrical activity. Ablation of tissue for ventricular tachycardia may be performed using RF energy delivered by an electrode positioned at the tip of an ablation catheter. Typically, the lesions formed by the ablation tip must extend deeply into the tissue and so good contact between the tip electrode and the tissue is important.

In patients experiencing atrial fibrillation and ventricular tachycardia, it is often desirable to map the electrical activity of the cardiac tissue in order to determine the location of the irregular electrical activity so that ablation procedures may be carried out at the appropriate location. One type of mapping catheter utilizes an expandable basket, plaque, helix, coil, or other structure positioned at the distal end of a catheter and a plurality of electrodes carried by the expandable structure.

The expandable structure is initially in a collapsed condition and is fed via the patient's vessels into the chamber of the heart which is to be mapped. Once inside the chamber, the expandable structure is released or moved into its expanded condition and it is positioned such that the electrodes are in contact with the cardiac tissue within the chamber. The electrical activity at each electrode site is monitored and maps showing the electrical activity at various points within the chamber may be produced.

As with ablation procedures, better results are achieved during endocardial mapping procedures if the mapping electrodes are securely supported against the endocardial tissue. If insufficient contact is made between the electrodes and the tissue, the electrical activity of the tissue beneath those electrodes will not be properly recorded.

Procedures and devices for ablating and/or mapping endocardial tissue are therefore desired which utilize catheters having sufficient flexibility and maneuverability to allow introduction of the electrodes into the cardiac chamber with minimal tissue trauma, but which hold the mapping and/or ablation electrodes securely against the target tissue which is to be mapped and/or ablated.

SUMMARY OF THE INVENTION

The present invention is a shapable catheter device which may be used for mapping and/or ablating endocardial tissue or other body tissue or for other medical procedures. The apparatus includes an elongate catheter having a lumen extending longitudinally through it. A core wire is insertable into the catheter via the lumen. The core wire includes a pre-shaped region which is formed of a superelastic material and which is bent into a predetermined shape.

The catheter includes a proximal section which is sufficiently rigid to straighten the core wire when the core wire is disposed within the proximal section. The catheter also includes a distal section which has significantly greater flexibility than the proximal section.

During use, the catheter is introduced into a body cavity such as a cardiac chamber, and the core wire is inserted into the catheter lumen. As the pre-shaped section of the core wire passes through the proximal section of the catheter, the rigidity of the proximal section causes the pre-shaped region of the core wire to straighten. When the pre-shaped region of the core wire enters the flexible distal section of the catheter, the pre-shaped region of the core wire deforms the distal section of the catheter into the predetermined shape.

In the preferred embodiment, electrodes are carried by the distal section of the catheter. During use, these electrodes are positioned in contact with tissue lining the body cavity and are used to ablate the tissue and/or to map the electrical activity of the tissue. A pull wire may additionally be provided to allow the user to cause deflection at a distal portion of the catheter.

BRIEF DESCRIPTION OF THE DRAWINGS

FIGS. 3A, 3B, 4 and 5B are side elevation views of four embodiments of core wires according to the present invention.

FIG. 5A is an end view of the spiral core wire of FIG. 5B.

FIG. 5C is an end view of the catheter of FIG. 1 following insertion of the spiral core wire of FIGS. 5A and 5B into the catheter.

FIGS. 22 through 25 are side elevation views of the distal portion of the catheter of FIG. 17, showing the distal portion configured into various shapes using the pull wire and shaped core wire alone or in combination.

DETAILED DESCRIPTION OF EXEMPLARY EMBODIMENTS

First Embodiment

The present invention is comprised generally of a catheter 10 and a pre-shaped core wire 12 which is receivable within the catheter to cause the catheter to form into the shape of the core wire 12.

Figure 1:
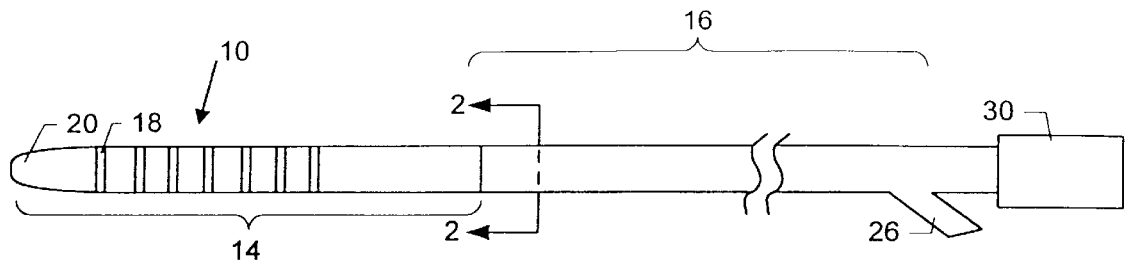
FIG. 1 is a side elevation view of a shapable catheter according to the present invention.

Referring to FIG. 1, the catheter 10 is an elongate shaft having a distal section 14 and a proximal section 16. A plurality of electrodes 18 are mounted to the distal section 14. Electrodes 18 may be conventional ring-type electrodes, or spaced conductive strips or bands formed on the surface of the catheter 10. Alternatively, the electrodes may be provided in combination with a electrolytic solution delivery system as will be described with respect to the embodiment of FIGS. 9–12.

Catheter 10 includes a tip 20 at its distal end. An additional electrode may be mounted to the tip 20.

Figure 2:
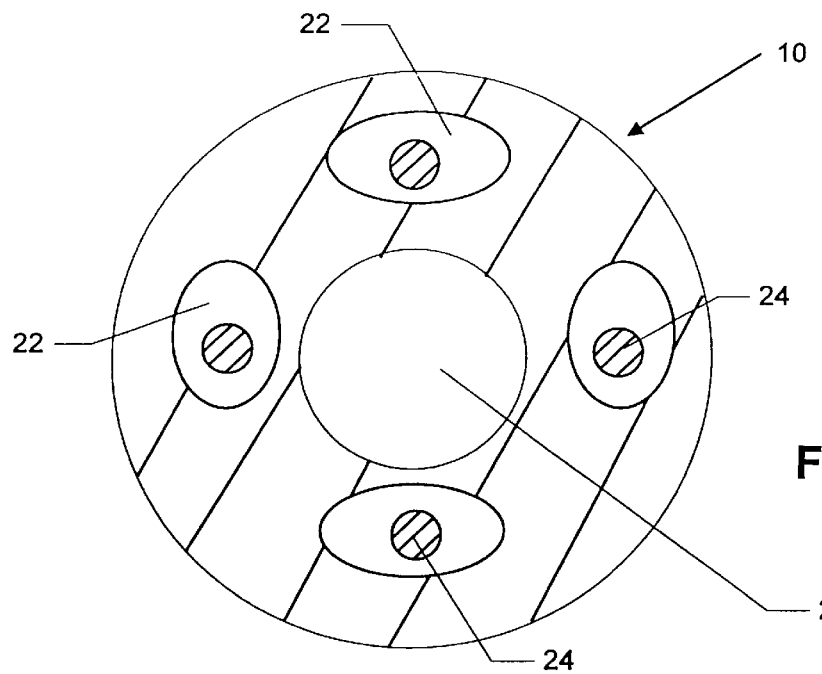
FIG. 2 is a cross-section view of the catheter of FIG. 1, taken along the plane designated 1-1 in FIG. 1.

Referring to FIG. 2, a plurality of lumens 22 extend longitudinally from the distal section 14 of the catheter 10 to the proximal section 16. Lead wires 24, which are electrically coupled to the electrodes 18, extend through the lumens 22 and terminate at an electrical connector 26 (FIG. 1) located at the proximal section 16. Connector 26 is attachable to an energy source, such as Model 8002 RF Generator which is available from Cardiac Pathways Corporation, Sunnyvale, Calif., for delivering energy to the electrodes. Connector 26 may alternatively or additionally be connectable to an endocardial mapping system such as Model 8100 Arrhythmia Mapping System available from Cardiac Pathways Corp., Sunnyvale, Calif.

A center lumen 28 also extends longitudinally through the catheter 10, preferably along the central axis of the catheter. During use, the core wire 12 is passed through the center lumen 28 as will be described in detail below. At the catheter's proximal end, center lumen 28 opens into a port 30 through which the core wire 12 is inserted during use.

The center lumen 28 may have a circular cross-section as shown in FIG. 2. Alternatively, both the center lumen 28 and the core wire 12 may have oblong cross-sections (see, for example, core wire 12c and lumen 28a in FIG. 10) to prevent rotation of the core wire within the lumen 28 during use. Such elongate cross-sections are further useful in that they allow for preferential bending of the catheter. In other words, referring to FIG. 10, the oblong cross-section of the catheter 10a allows bending of the catheter to be effectively limited to be across a preferential bending plane, i.e., across long sides 48 of the catheter 10a.

Catheter 10 is preferably constructed of a thermoplastic polymer, polyamid ether, polyurethane or other material having similar properties. A stainless steel braid (not shown) is preferably embedded in the wall of the main shaft by means conventionally known in the art. The inclusion of the braid improves the torque characteristics of the catheter 10 and thus makes the catheter easier to maneuver through a patient's vessels and heart.

The material forming the distal section 14 of the catheter 10 is selected to have a sufficiently low durometer or hardness (e.g., approximately 25–50 Shore D) to permit the distal section 14 to be highly flexible. In contrast, the proximal section 16 is formed of a higher durometer material (e.g., approximately 55–80 Shore D) and thus is fairly rigid.

Figure 3A:
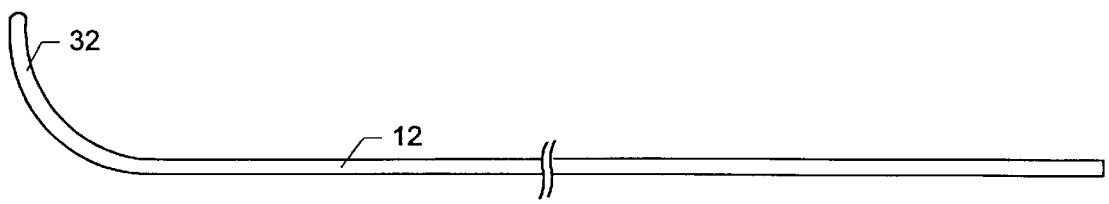

Referring to FIG. 3A, core wire 12 is an elongate wire formed of a superelastic material such as Nitinol. Core wire 12 includes a pre-shaped section 32, preferably at its distal end. The pre-shaped section 32 may have the C-curve shown in FIG. 3A, or it may have one of numerous other shapes including the Z- or S-curve of the core wire 12a of FIG. 4, the spiral shape of the core wire 12b of FIGS. 5A and 5B, or the J-curve of the core wire 12d of FIG. 3B.

Figure 6A:
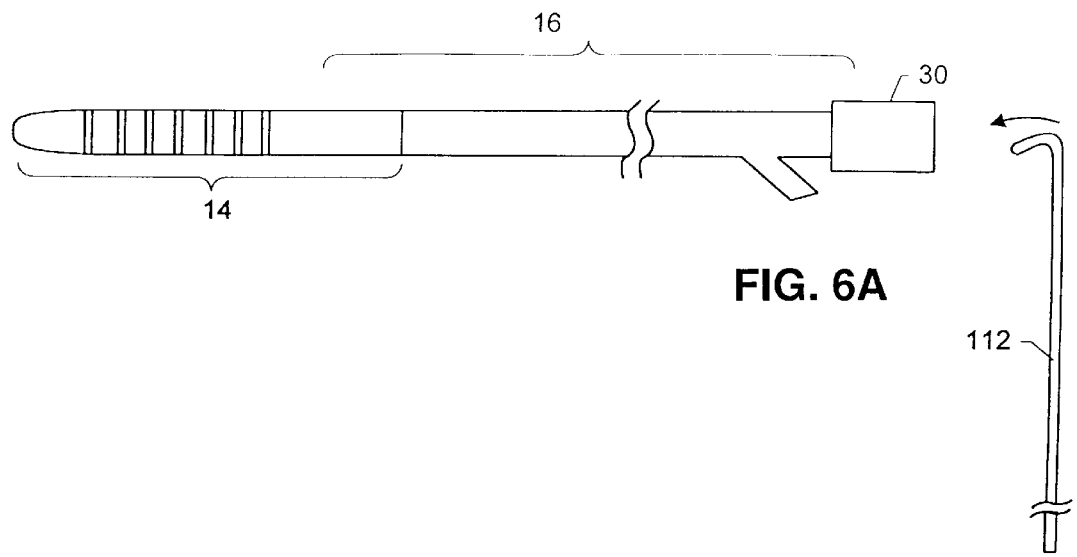
FIGS. 6A, 6B and 7 are a series of side elevation views showing insertion of a core wire according to the present invention into the shapable catheter of FIG. 1.
Figure 6B:
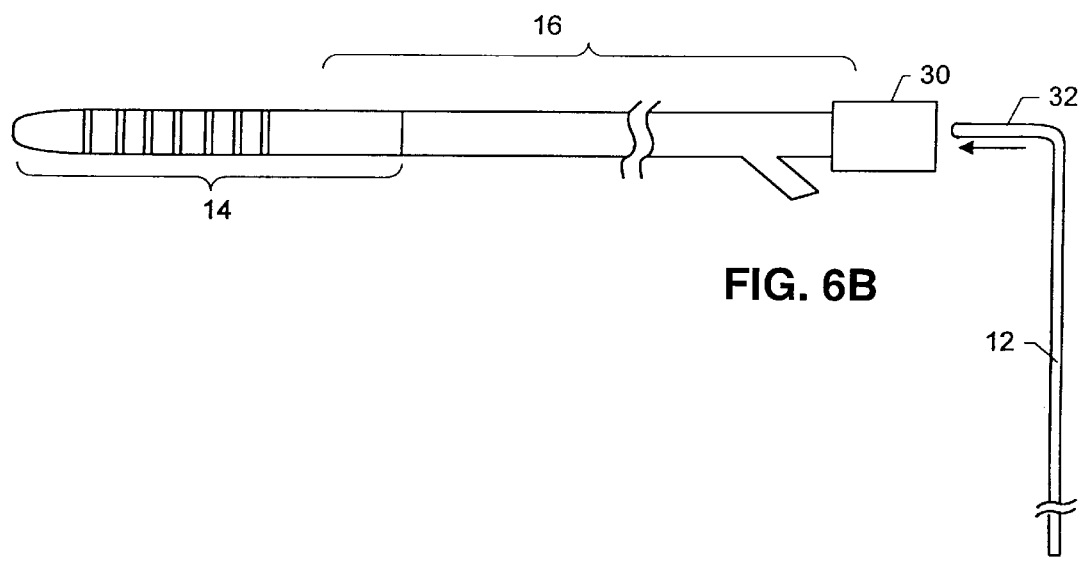
Figure 7:
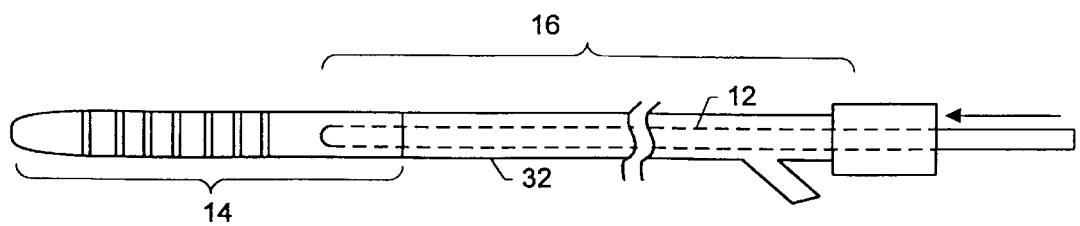
Figure 8A:
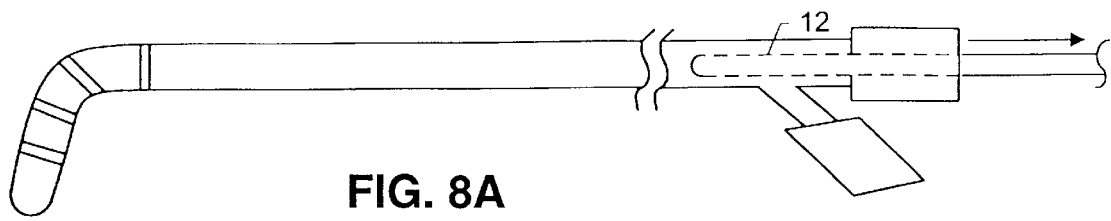
FIG. 8A is a side elevation view showing the catheter of FIGS. 6A, B and 7 following insertion of the core wire into the catheter.
Figure 8B:
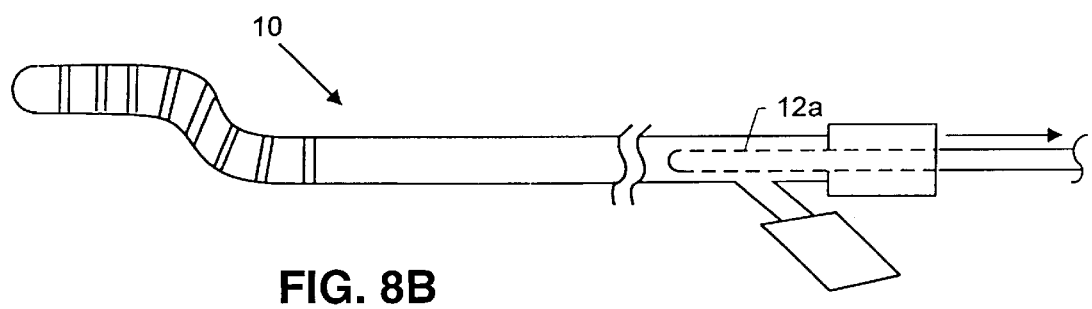
FIG. 8B is a side elevation view showing the catheter of FIGS. 6A, B and 7 following insertion of the core wire of FIG. 4 into the catheter.

When a core wire such as core wire 12 is introduced into the catheter 10 via port 30 as shown in FIG. 6, core wire 12 is initially straightened by the rigidity of proximal section 16 as illustrated in FIG. 7. As the core wire 12 passes into distal section 14, it is unrestricted by the flexible material of the distal section 14. The characteristics of the superelastic core wire material thus cause the unrestricted core wire to return to its pre-formed shape and to cause the distal section 14 of the catheter 10 to take the shape of the core wire. See, e.g., FIGS. 8A and 5C.

Thus, the shape of the core wire is selected based on its suitability for the procedure for which the catheter 10 is to be used. During use, core wires 12 and 12a (FIGS. 3A, 3B, 4, 8A, and 8B) can cause the catheter 10 to lay along the atrial wall of the heart to create a linear lesion. Spiral core wire 12b (FIGS. 5A and 5B) forms the catheter into a planar mapping plaque (FIG. 5C) which may be positioned into contact with the endocardium for mapping. Innumerable planar or non-planar core wire shapes may be used without exceeding the scope of the present invention.

Use of the shapable catheter 10 according to the present invention will next be described.

First, catheter 10 is inserted through a patient's vasculature to position distal section 14 within the cardiac chamber in which mapping or ablation is to be performed. Introduction of the catheter through the vasculature may be facilitated by first introducing a superelastic guiding core wire, such as core 112 shown in FIG. 6A, into the catheter 10. Guiding core 112 preferably has a small hook 132 at its distal end. This causes the distal portion 14 of the catheter 10 to substantially conform to the shape of the guiding core 112, thereby placing a small bend in the distal end of the catheter. This small bend is useful in preventing the catheter from passing into small side vessels and from catching on structures within the heart during its introduction into the heart.

Once the distal portion 14 of the catheter is situated within the desired chamber of the heart, guiding core 112 is withdrawn. Next, a core wire such as core wire 12 is selected, with the selected core wire shape depending on the region of the heart to be mapped or treated. The selected core wire 12 is inserted into center lumen 28, causing the distal section 14 to assume the pre-formed shape of the core wire 12.

Figure 14:
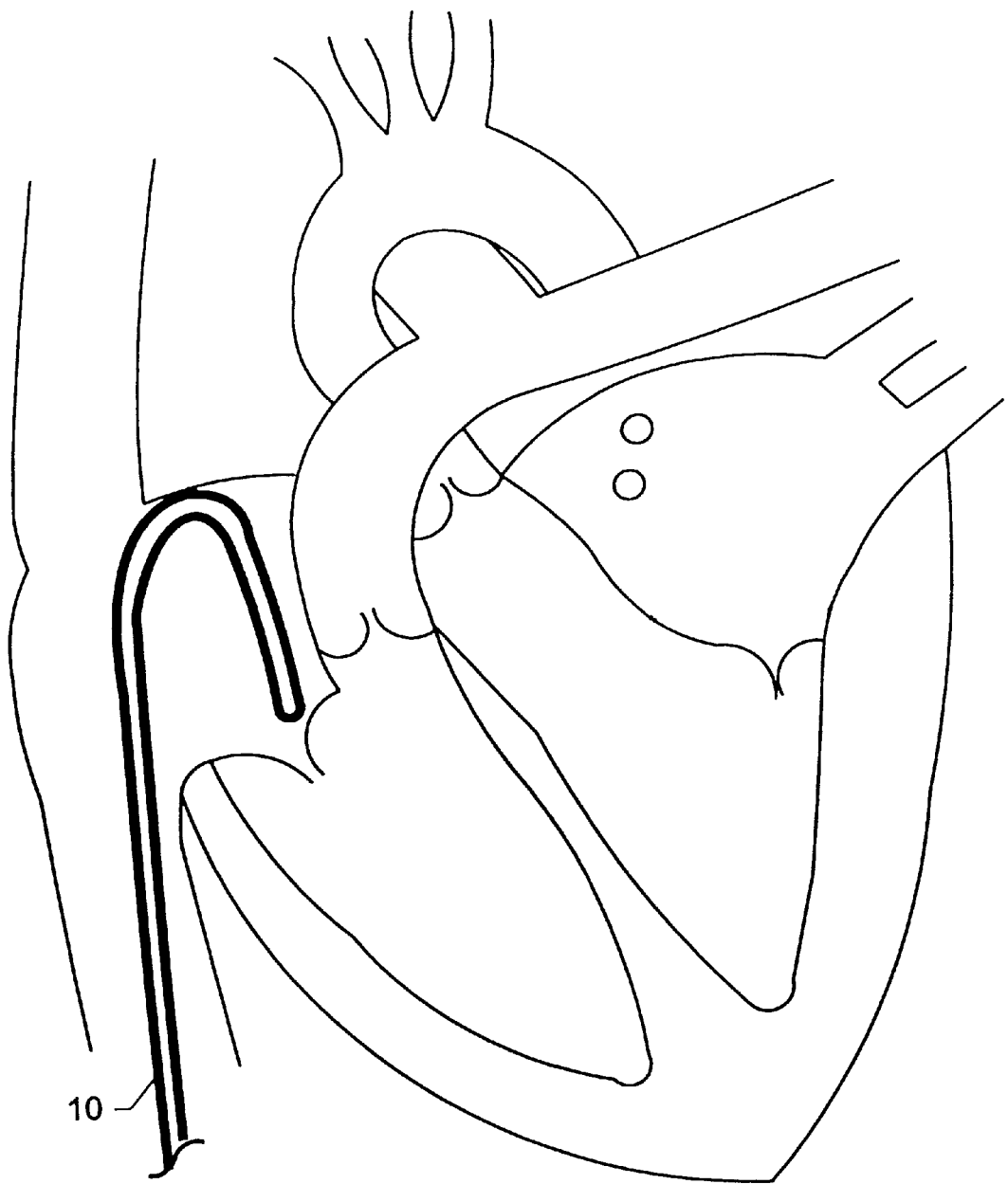
FIG. 14 is a representation of the interior of the heart illustrating the catheter of the present invention when positioned to create a lesion from the superior vena-cava to the tricuspid valve anulus.
Figure 15:
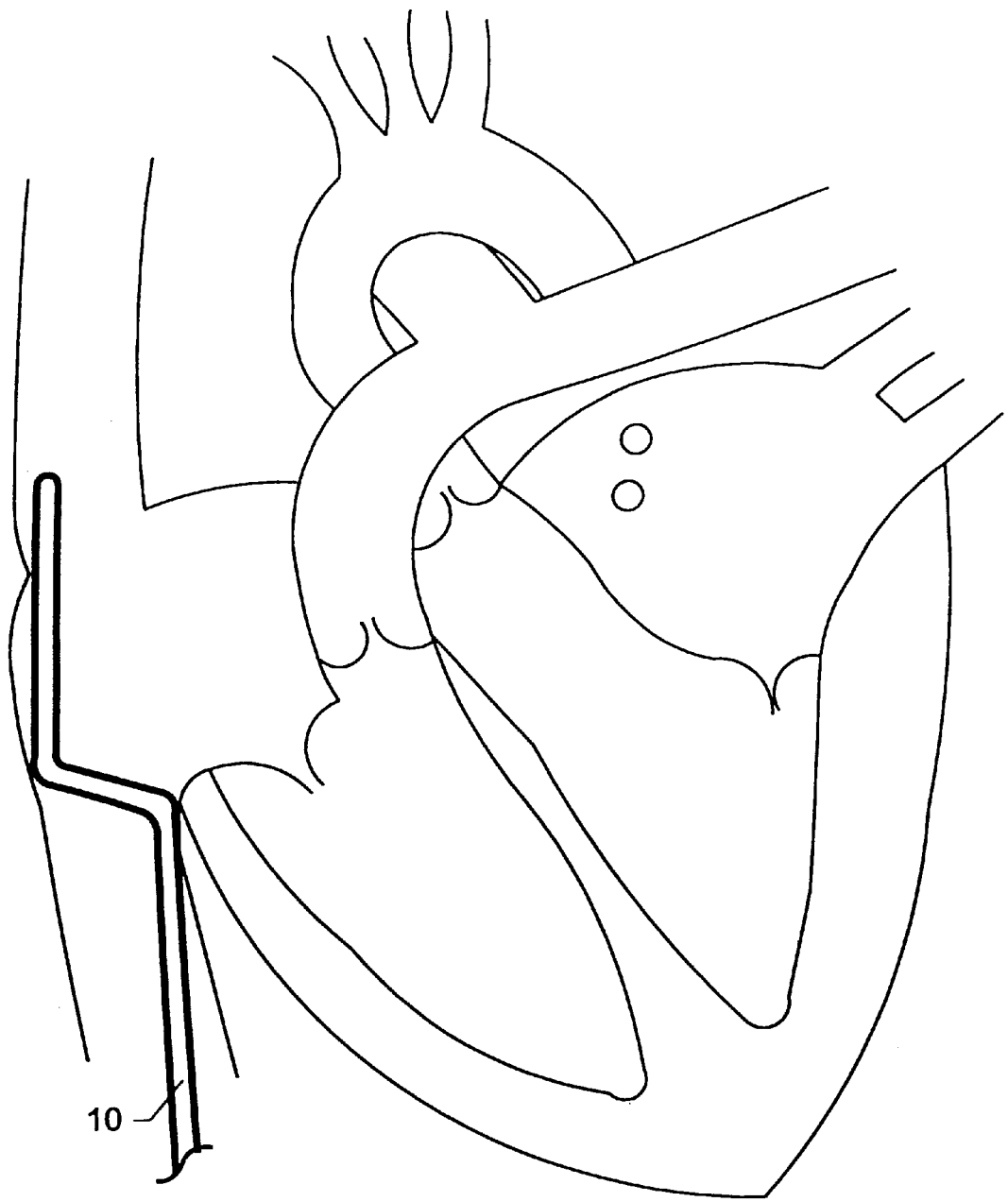
FIG. 15 is a representation of the interior of the heart illustrating the catheter of the present invention when positioned to create a lesion from the inferior vena-cava to the superior vena-cava.
Figure 16:
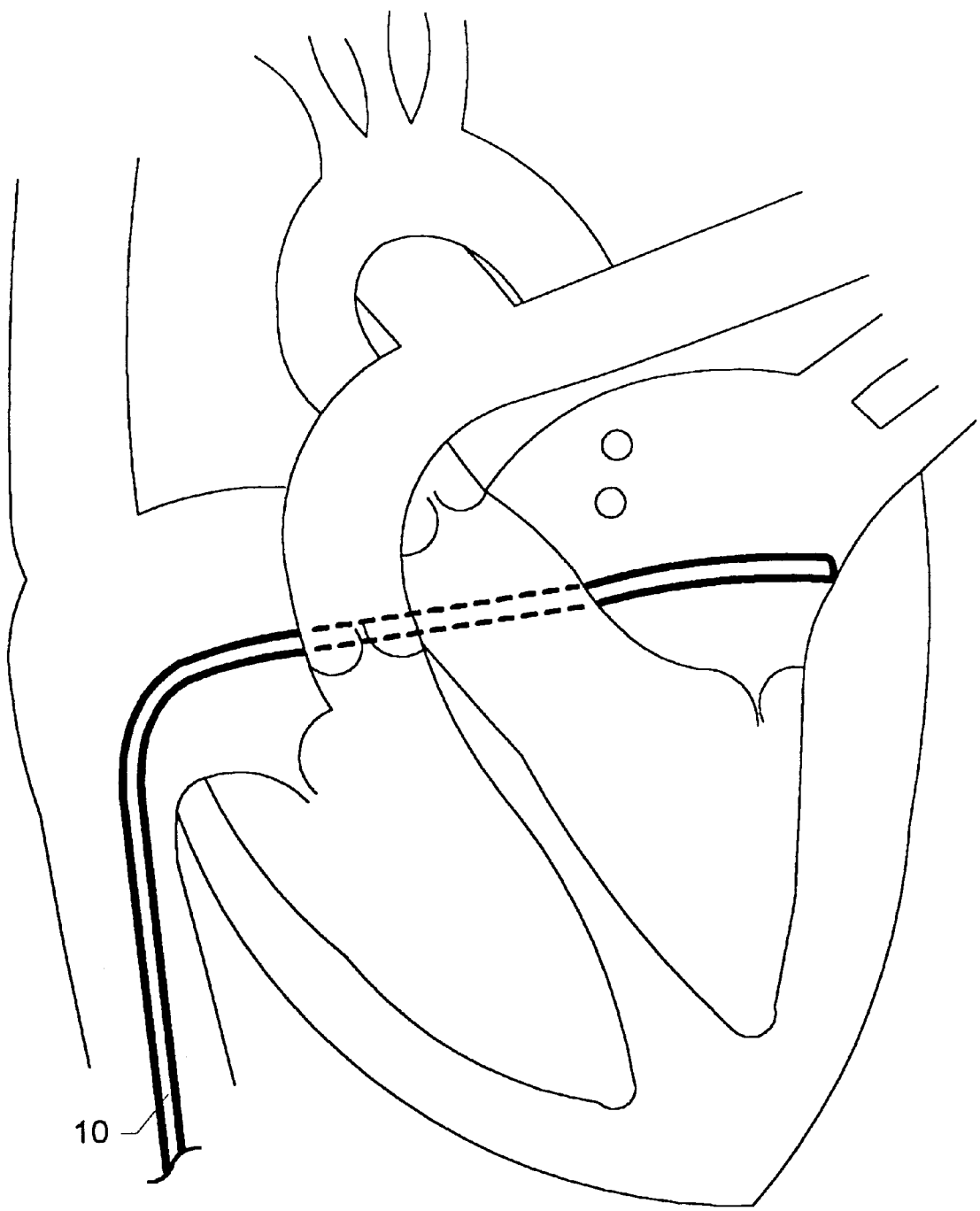
FIG. 16 is a representation of the interior of the heart illustrating the catheter of the present invention when positioned transseptally to create a lesion from the atrial septum to the mitral valve anulus.

The distal section 14 is positioned, preferably under fluoroscopy, against the tissue so that the electrodes 18 make contact with the target cardiac tissue. FIGS. 13–16 illustrate examples of catheter positions within the heart which may be achieved after a selected core wire has been inserted into the catheter and the catheter positioned against the target cardiac tissue. For example, a hook-shaped or J-shaped core wire such as core wire 12d of FIG. 3B may be inserted partially (FIG. 13) or fully (FIG. 14) into the catheter to give the catheter a shape that is useful for forming lesions from the inferior vena-cava to the tricuspid valve anulus (FIG. 13) or from the superior vena-cava to the tricuspid valve anulus (FIG. 14). Alternatively, the core wire 12a of FIG. 4 may be utilized as shown in FIG. 15 to shape the catheter for forming lesions from the inferior vena-cava to the superior vena-cava, or a core having an approximately 90° bend may be utilized as shown in FIG. 16 for creating a lesion from the atrial septum to the mitral valve anulus.

An RF generator and/or a mapping system is connected to the catheter 10 via connector 26, and a mapping and/or ablation procedure is performed.

Once the procedure is completed, the core wire 12 is removed from the catheter 10. The rigid proximal section 16 of the catheter 10 temporarily straightens the core wire 12 into the condition shown in FIG. 7 as the core wire is withdrawn, thus facilitating removal of the core wire.

One significant advantage of the subject invention is that multiple core wires of differing shapes may be used during a single procedure. This allows the physician the ability to change the geometry of the catheter 10 without having to remove the catheter from the heart and to re-insert a new catheter through the patient's vasculature. Instead, the physician may remove first core wire 12 from the catheter 10, as indicated by the arrow in FIG. 8A., following an ablation and/or mapping procedure, and then replace it with a second core wire, such as core wire 12a, as indicated by the arrow in FIG. 8B, to re-shape the catheter 10. The re-shaped catheter 10 is positioned into contact with the endocardium and a second mapping and/or ablation procedure is performed.

Second Embodiment

FIGS. 9–12 show an alternative catheter 10a according to the present invention which utilizes an electrode configuration in which an electrolytic solution is used to create a conductive path between the electrodes and the endocardial tissue. This configuration is particularly useful for creating transmural linear lesions during the "maze procedure." Catheters utilizing electrode configurations of this type are described and claimed in pending U.S. application Ser. No. 08/611,656, entitled APPARATUS AND METHOD FOR LINEAR LESION ABLATION, which is incorporated herein by reference.

Figure 9:
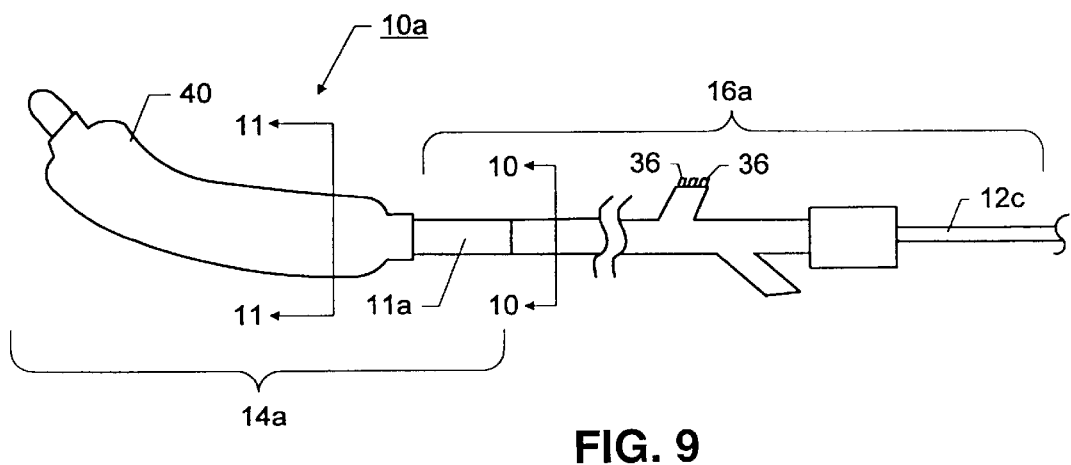
FIG. 9 is a side elevation of an alternative embodiment of a shapable catheter according the present invention, in which an electrolytic solution is used to create a conductive path between the electrodes and the endocardial tissue.
Figure 10:
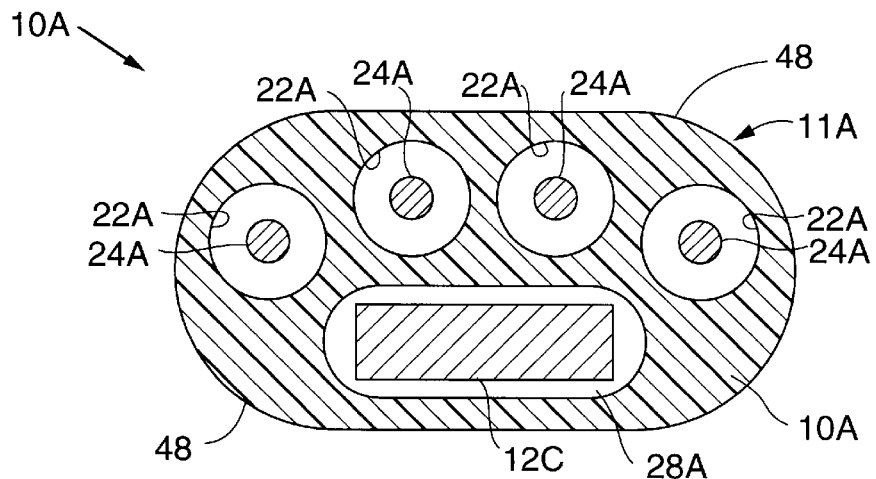
FIG. 10 is a cross-section view of the catheter shaft of the embodiment of FIG. 9, taken along the plane designated 10—10 in FIG. 9.

Referring to FIG. 9, catheter 10a includes distal and proximal sections 14a, 16a which are made of materials similar to those used for the catheter 10 of the embodiment of FIG. 1. Lumens 22a and core wire lumen 28a (FIGS. 10 and 11) extend longitudinally through catheter shaft 11a. The lumen 22a are fluidly coupled to fluid ports 36 (FIG. 9) located at proximal section 16a. A core wire 12c is insertable into the core wire lumen 28a as described with respect to the embodiment of FIG. 1.

Figure 11:
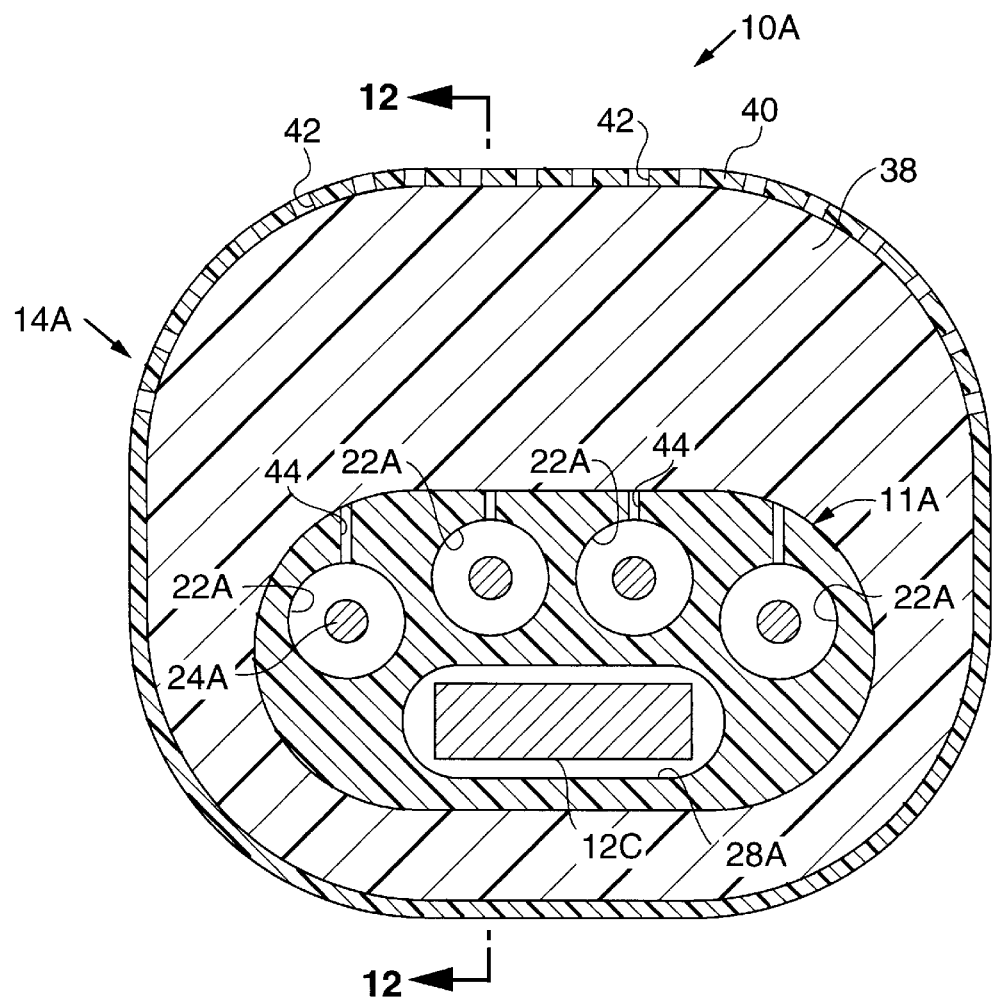
FIG. 11 is a cross-section view of the proximal section of the embodiment of FIG. 9, taken along the plane designated 11—11 in FIG. 9.
Figure 12:
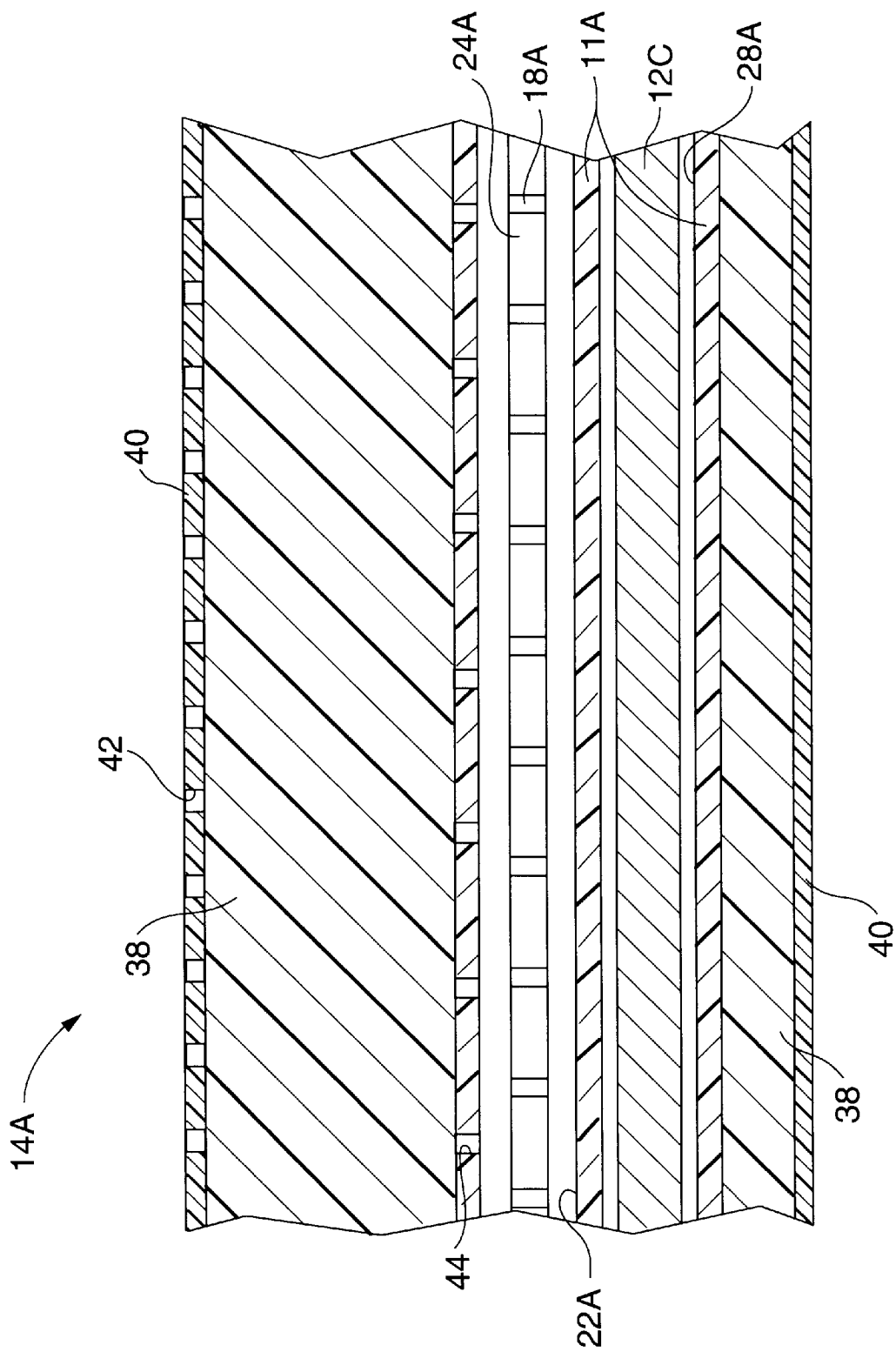
FIG. 12 is a cross-section view of the proximal section of the embodiment of FIG. 9, taken along the plane designated 12—12 in FIG. 11.
Figure 13:
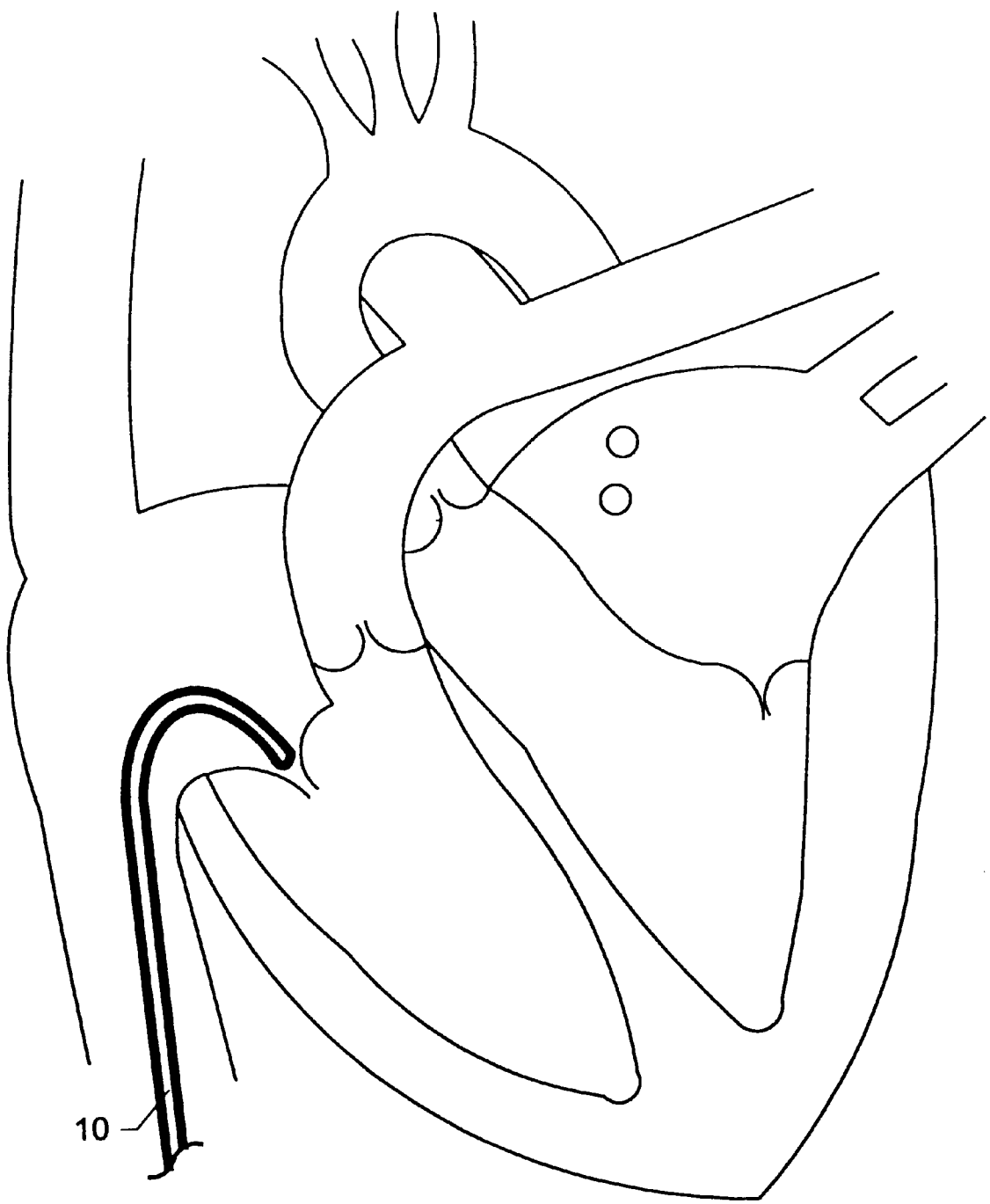
FIG. 13 is a representation of the interior of the heart illustrating the catheter of the present invention when positioned to create a lesion from the inferior vena-cava to the tricuspid valve anulus.

Referring to FIGS. 11 and 12, a deformable member (or "foam layer") 38 is formed in an eccentric configuration at the distal section of catheter 11a such that it is thicker on one side of the catheter 10a than it is on the other side. During use, the side of the distal section having the thick region of foam is positioned against the target tissue which is to be ablated. Foam layer 38 is formed of open cell polyurethane, cotton-like material, open-cell sponge, hydrogels, or other foam-like materials or materials which are permeable by conductive fluids and which exhibit some compressibility. The foam layer need not be segmented but it has been found that RF energy is more effectively channeled to the cardiac tissue by providing the foam in segments rather than in a continuous piece.

Foam layer 38 is enclosed within a fluid impermeable covering 40 which includes a plurality of tiny holes 42. Covering 40 is preferably formed of heat shrink polyethylene, silicone, or other polymeric materials and is preferably held in place by heating its ends to cause the heat shrink material to melt onto the catheter shaft. Covering 40 may also be a dip coating formed on the foam surface.

Holes 42 in the covering 40 may be formed only in the side of the covering at which the foam 38 is thickest. This helps to focus the RF energy onto the target tissue within the heart.

Holes 44 extend from fluid lumen 22a through the catheter shaft 11a to the foam layer 38. The holes 44 are located at the side of the catheter 10a at which the thickened foam region is located to permit the flow of conductive fluid from the fluid lumen 22a to the foam 38 and then through the holes 40 in the covering.

Rather than utilizing ring electrodes of the type described above, the second embodiment utilizes conductive wires 24a or flat conductive ribbons, each of which is covered by an insulated coating. Exposed electrode regions 18a (FIG. 12) that are stripped of insulative material are spaced along the portion of the wires 24a that is located within the distal section 14a.

During use, the distal section of the catheter 10a is positioned adjacent to the body tissue which is to be ablated. RF energy is delivered to the electrodes while saline or other conductive fluid is simultaneously delivered through the lumen 22a. The conductive fluid passes the electrodes 18a within the lumen 22a. It further flows via holes 44 through the foam 38 and through the holes 42 in the covering into contact with the body tissue, thereby improving the coupling of the RF energy from the electrodes to the tissue and improving the efficiency of the ablation of the tissue. Use of the shapable aspects of the catheter 10a is the same as that described with respect to the catheter 10a of FIG. 1 and need not be repeated.

Third Embodiment

A third embodiment of a shapable catheter according to the present invention is shown in FIGS. 17–25. The third embodiment utilizes a pull wire which allows the catheter shape to be controlled by the pull wire and shaped core wire either alone or in combination. The third embodiment will be described to utilize fluidly coupled ablation electrodes such as those utilized in the second embodiment. However, it should be appreciated that the third embodiment may be an ablation, mapping, or mapping/ablation catheter and it may utilize the ring electrodes of the embodiment of FIG. 1 for mapping and/or ablation, or other electrode configurations, without departing from the scope of the invention.

Figure 17:
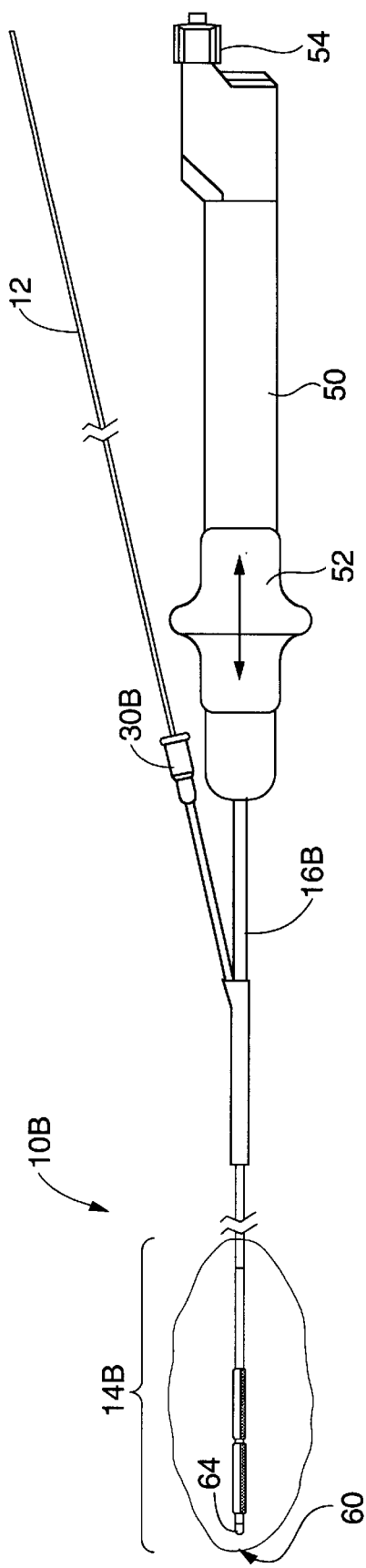
FIG. 17 is a side elevation view of a third embodiment of a shapable catheter according to the present invention which further utilizes a pull wire for deflection.

Referring to FIG. 17, catheter 10b of the third embodiment includes distal and proximal sections 14b, 16b which are made of materials similar to those used for the catheter 10a of the embodiment of FIG. 9. Port 30b for receiving a core wire 12 is angularly connected to the catheter body. The catheter includes a handle 50 having a sliding member 52 which, as described, actuates a pull wire disposed within the catheter 10b. A connector 54 at the proximal end of the handle is attachable to a source of electrolytic solution and a source of RF energy.

Figure 18:
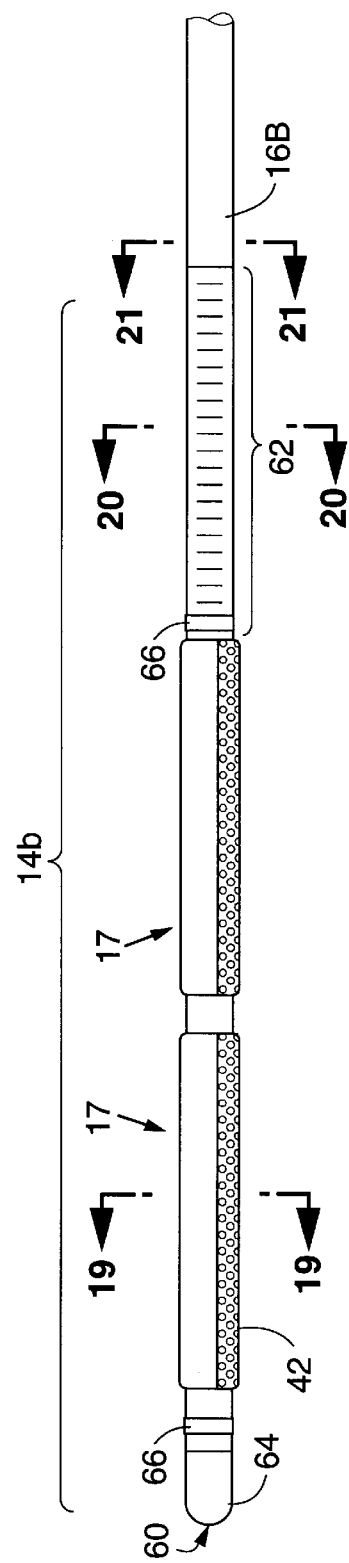
FIG. 18 is a side elevation view of the distal portion of the catheter of FIG. 17.
Figure 19:
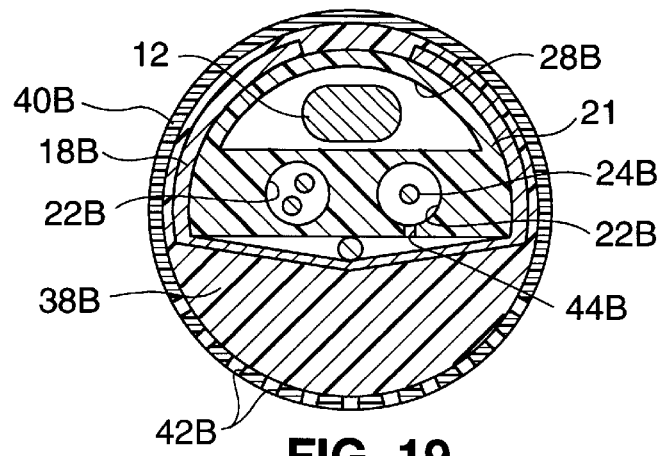
FIG. 19 is a cross-section view of the ablation section of the catheter of FIG. 17, taken along the plane designated 19—19 in FIG. 18.
Figure 20:
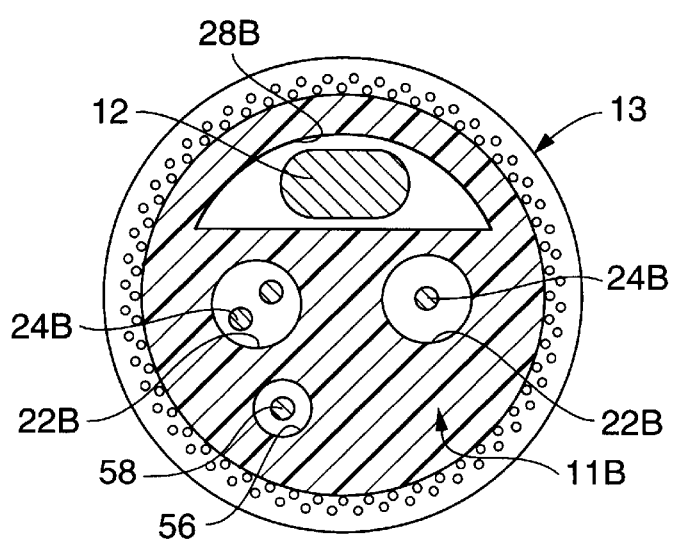
FIG. 20 is a cross-section view of the distal portion of the catheter of FIG. 17, taken along the plane designated 20—20 in FIG. 18.
Figure 21:
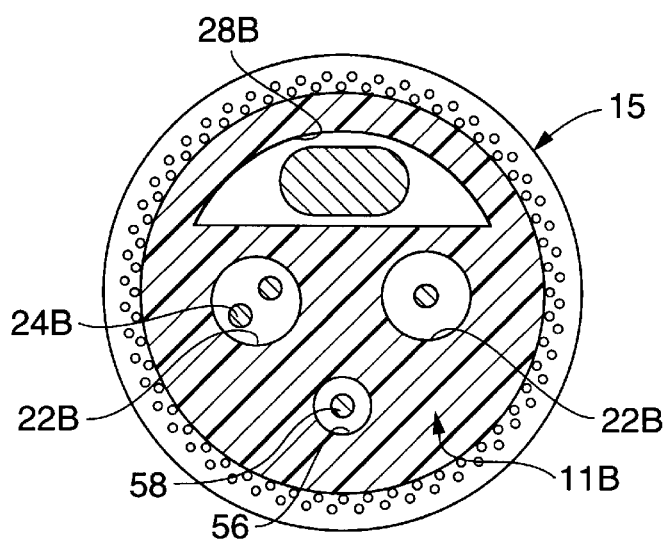
FIG. 21 is a cross-section view of the proximal portion of the catheter of FIG. 17, taken along the plane designated 21—21 in FIG. 18.

Referring to FIG. 18, as with the first and second embodiments, the distal section 14b of the catheter 10b is designed to be more flexible than the proximal section 16b.

This difference in flexibility can be achieved by varying the hardness (durometer) of the polymer used in each section. The distal section would be formed of a material selected to have a sufficiently low durometer of hardness (e.g., approx. 25–50 Shore D) to permit the distal section 14b to be highly flexible. In contrast, the proximal section 16b is formed of a higher durometer material (e.g., approx. 55–80 Shore D) and thus, fairly rigid. Both the proximal 16b and distal section 14b may also contain stainless steel or polymer braid wire 13, 15 or ribbon to give the device more torsional stiffness to help position the device in the anatomy. Other methods to achieve a stiffness transition can also be used and still be in the scope of this invention.

A pair of ablation pads 17 are located on the distal section 14b. Each pad 17 is positioned over distal tubing 21 which includes lumens 22b and 28b that are continuous with the corresponding lumens in the more proximal sections of the catheter. Each pad 17 is comprised of a plurality of spaced ring electrodes 18b (FIG. 19), a deformable member or foam layer 38b and a fluid impermeable covering 40b that is provided with a plurality of tiny holes 42b that permit the flow of electrolytic solution out of the ablation pads 17.

Foam layer 38b is preferably formed of open cell polyurethane, cotton-like material, open-cell sponge, hydrogels, or other foam-like materials or materials which are permeable by conductive fluids and which exhibit some compressibility. The foam layer need not, but may be, segmented as described with respect to the second embodiment.

Covering 40b is preferably formed of polyethylene, silicone, or other polymeric materials and is preferably held in place by heating its ends to cause the it material to melt onto the catheter shaft. Covering 40b may also be a dip coating formed on the foam surface.

The foam layer and covering are preferably arranged such that the holes 42b in the covering are on one side of the catheter 10b. During use, this allows RF energy to be focused in the region of tissue which lies under the portion of the catheter on which the holes are located.

The catheter 14b may additionally include a distal tip electrode 64 for mapping and/or ablation. Moreover, ring electrodes 66 may be positioned on distal section 14b distally and proximally of the pads 17. The ring electrodes 66 may be utilized in a variety of ways, including for mapping, to evaluate lesions formed in the tissue immediately after ablation has been performed, and/or to assess contact between the ablation section of the catheter and the tissue.

Lumens 22b and core wire lumen 28b extend longitudinally through the catheter shaft. The lumen 22b are fluidly coupled to connector 54 (FIG. 18) located at proximal section 16b. The core wire 12 is insertable into the core wire lumen 28b via the port 30b (FIG. 17).

Holes 44b extend from fluid lumen 22b through the catheter shaft 11b to the foam layer 38b. The holes 44b permit the flow of conductive fluid from the fluid lumen 22b to the foam 38b and then through the holes 42b in the covering.

The third embodiment utilizes insulated conductive wires 24b (FIGS. 20 and 21) or flat conductive ribbons, each of which is covered by an insulated coating and coupled to ring electrodes 18b, or to the tip electrode 64 or the ring electrodes 66.

In place of ring electrodes 18b for fluid coupled ablation, the wires 24b may be provided with exposed electrode regions (such as regions 18a of the second embodiment in FIG. 12) that are stripped of insulative material are spaced along the portion of the wires 24b that is located within the distal section 14b.

Referring again to FIGS. 20 and 21, a pull wire lumen 56 extends through the catheter body 11b. A pull wire 58 extends from the handle 52 (FIG. 17), through the lumen 56, and is secured at a distal location within the catheter body 11b. Movement of handle 52 longitudinally as indicated by the arrow in FIG. 17 causes longitudinal movement of the pull wire within the lumen 56.

The location at which the pull wire 58 is attached to the interior of the catheter body 11b is dependent upon the effect which the pull wire is desired to have. For example, if it is desired that application of tension on the pull wire results in bending a large portion of the distal section 14b, then the pull wire is secured to the distal portion of the catheter body, preferably at the distal tip 60. Because the pull wire is offset from the center axis of the catheter body 11b, longitudinal movement of the handle 52 in the proximal direction causes the pull wire 58 to pull the distal tip 60 in a proximal direction to cause bending of the catheter 10b, while longitudinal movement of the handle in the distal direction relieves the tension on the pull wire 58 and thus on the distal tip 60.

The pull wire 58 may be alternatively attached to the catheter body 11b at a more proximal region of distal section 14b, such that tension on the pull wire results in deflection of the distal portion 14b within the region designated 62 in FIG. 18.

The third embodiment according to the present invention allows the pull wire and shaped core wire to be used separately or together as needed for particular applications. For example, by positioning a core wire having a shape similar to the core wire 12a of FIG. 4, in the distal portion of catheter 10 b, the catheter may be shaped as shown in FIG. 22. If the catheter is provided to have pull wire 58 attached near the catheter's distal tip, withdrawing the pull wire 58 while the core wire 12a is positioned in the distal portion 14b can produce a shape such as that shown in FIG. 23.

Figure 24:
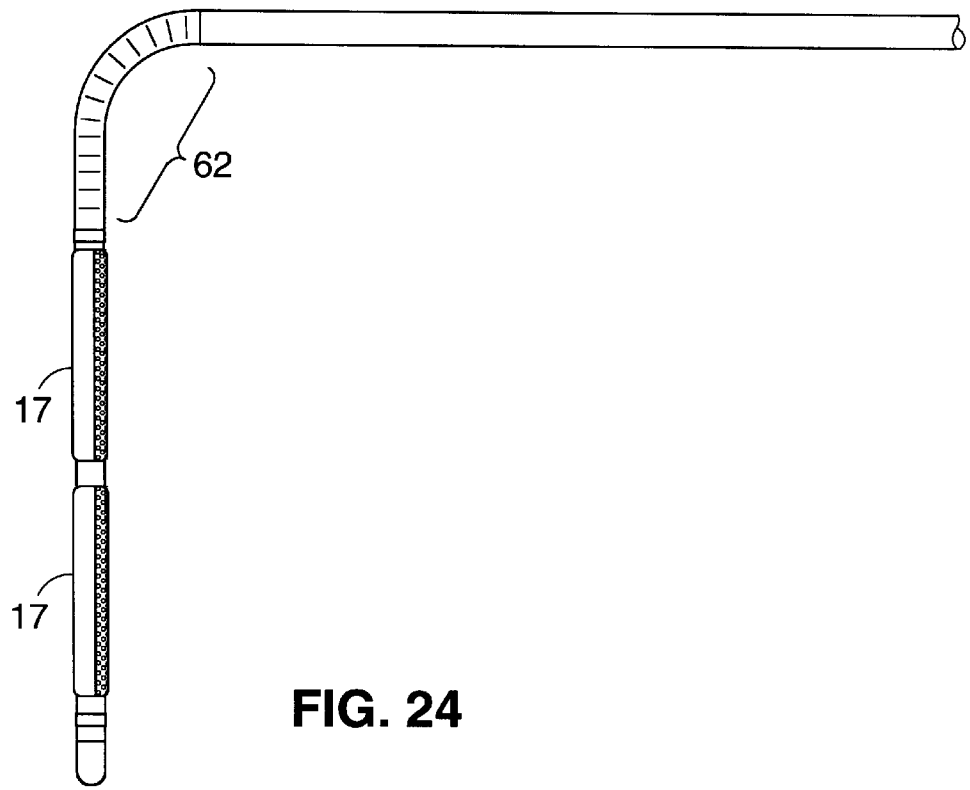
Figure 25:
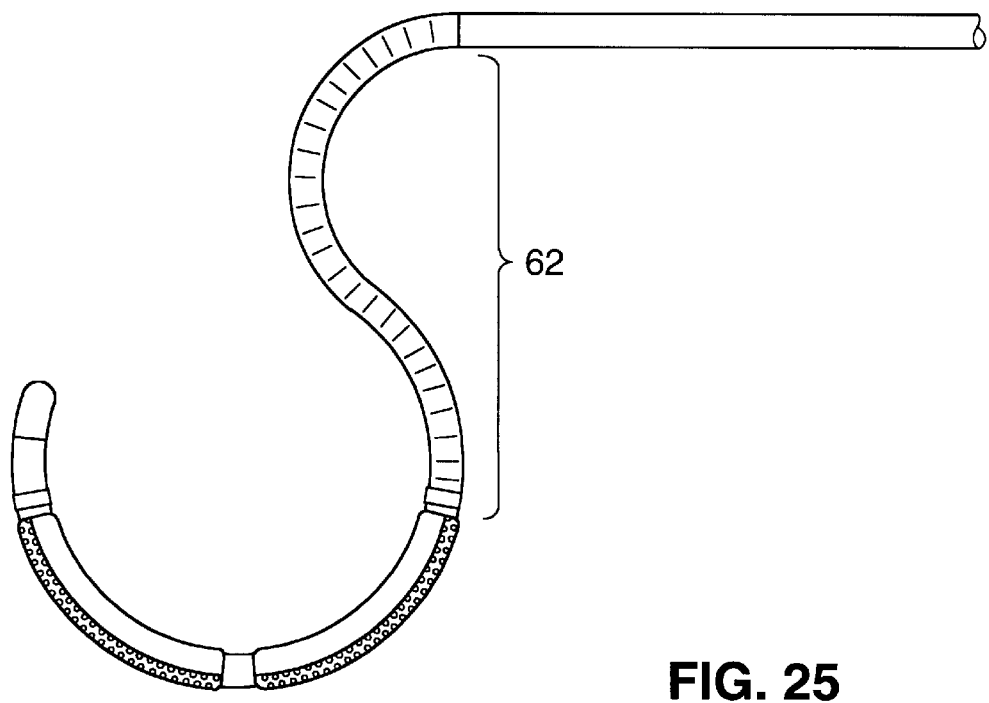

The catheter configuration shown in FIG. 24 may be achieved if the pull wire is attached to distal portion 14b at a location proximal of the pads 17 and is withdrawn without a shaped core in place. If this use of the pull wire is combined with a core such as core 12a, the configuration of FIG. 25 may be achieved.

The catheter 10b may be used clinically in a variety of ways. For example, the catheter 10b may be inserted into the heart without first inserting a core wire into the lumen 28b or alternatively with a straight core wire in the lumen 28b. During tip placement, tension may be placed on the pull wire to stiffen and deflect the distal portion 14b to facilitate steering. The distal tip 60 is positioned in a desired location within the heart, such as in the pulmonary veins as would be done in an ablation procedure for Atrial Fibrillation.

Once the distal tip is positioned as needed, tension on the pull wire 58 is released to allow the distal portion 14b to be flexible. A shaped core wire is inserted into the lumen 28b, causing the catheter to assume the desired shape with the distal tip 60 remaining in the desired position. The shaped core wire is oriented to force the pads 17 of the catheter 10b against the wall of the atrium, allowing RF formation of a linear lesion using the pads while the distal tip remains anchored in place.

In another example of use of a catheter (such as catheter 10b) utilizing a pull wire and shaped core in combination, the physician may position the catheter in the desired chamber of the heart prior to inserting a core wire. With the catheter positioned within the desired chamber, a shaped core such as the helical coil 12b of FIGS. 5A and 5B is advanced through lumen 28b into distal portion 14b of the catheter. The core wire 12b, which has a spiral 32b perpendicular to the axis of the core wire shaft, creates a spiral pattern of electrodes having the shape of the core wire 12b to create a mapping or ablation array that could be steered by the user using pull wire 58. The catheter may be provided with an array of ring electrodes such as those shown in FIG. 1 for this purpose. For this application, it is preferable for the pull wire to be attached to the catheter body 11b towards the proximal end of the distal portion 14 to cause the pull wire to induce deflection in the region 62.

Three embodiments of shapable catheters and three embodiments of shapable catheter core wires have been described herein. It should be appreciated, however, that these embodiments have been given by way as example and are not intended to limit the scope of the appended claims. Moreover, although mapping and ablation have been given as exemplary applications of the present invention, the scope of the present invention is not limited to those applications, as the shapable catheter described herein is suitable for use in other medical applications as well.

What is claimed is:

1. A shapable medical apparatus comprising, in combination:
   a core wire having a shaped distal portion with a predetermined non-linear shape;
   a catheter having a lumen proportioned to slidably receive the core wire, the catheter including a proximal section and a distal section, the core wire slidably receivable within the lumen such that when the core wire is advanced so that at least a portion of the shaped portion is within the distal section of the catheter, the catheter is deformed to approximate the non-linear shape of the portion of the shaped portion of the core wire that is within the distal section of the catheter; and
   a pull wire within the catheter, the pull wire slidable to cause deflection of the distal section of the catheter.

2. The apparatus of claim 1 further comprising a plurality of electrodes mounted on the distal section of the catheter.

3. The apparatus of claim 1, further comprising:
   a source of ablation energy;
   an ablation section on the distal section of the catheter, the ablation section including at least one electrode coupled to the source of ablation energy, and a fluid port for delivering conductive fluid into contact with at least one of the electrodes and to cause said fluid to create a conductive path between said at least one electrode and the tissue when said at least one electrode is positioned adjacent body tissue.

4. The apparatus of claim 3 wherein the ablation section further includes a fluid permeable deformable member at least partially covering said at least one of the electrodes.

5. The apparatus of claim 4 wherein the deformable member includes a layer of foam material formed over said at least one of the electrodes.

6. The apparatus of claim 4, further comprising a covering on the deformable member, the covering formed of a material substantially impermeable to fluid, the covering including at least one opening sized to allow passage of fluid out of the covering.

7. The apparatus of claim 2 wherein the electrodes include electrodes configured to measure electrical activity of adjacent body tissue.

8. The apparatus of claim 1, wherein the core wire is a first core wire and wherein the apparatus further comprises a second core wire having a distal portion with a second predetermined non-linear shape, the second predetermined shape being different from the predetermined shape of the first core wire, and wherein the second core wire is slidably receivable within the lumen.

9. The apparatus of claim 1 wherein the predetermined shape is a spiral.

10. The apparatus of claim 1 wherein the predetermined shape is an approximate Z-curve.

11. The apparatus of claim 1 wherein the predetermined shape is an approximate C-curve.

12. The apparatus of claim 1 wherein the predetermined shape is an approximate J-curve.

13. The apparatus of claim 1 wherein the catheter and core wire are configured for preferential bending across a preferential bend plane.

14. The apparatus of claim 1 wherein the catheter has an elongate cross-section.

15. The apparatus of claim 1 wherein the core wire is formed of a superelastic material.

16. The apparatus of claim 15 wherein the superelastic material is Nitinol.

17. A shapable medical apparatus comprising, in combination:
   a core wire having a distal portion with a predetermined non-linear shape;
   a catheter having a lumen proportioned to slidably receive the core wire, the catheter including a proximal section and a distal section, the distal section having greater flexibility than the proximal section, the core wire slidably receivable within the lumen such that when the core wire is introduced into the proximal section of the catheter, said distal portion is substantially straightened by the proximal section of the catheter, and when said core wire is advanced so that at least a portion of the distal portion is within the distal section of the catheter, the catheter is deformed to approximate the non-linear shape of the portion of the distal portion of the core wire that is within the distal section; and
   a pull wire within the catheter, the pull wire slidable to cause deflection of the distal section of the catheter.

18. The apparatus of claim 17 further comprising a plurality of electrodes mounted on the distal section of the catheter.

19. The apparatus of claim 17, wherein the core wire is a first core wire and wherein the apparatus further comprises a second core wire having a distal portion with a second predetermined non-linear shape, the second predetermined shape being different from the predetermined shape of the first core wire, and wherein the second core wire is slidably receivable within the lumen.

20. The apparatus of claim 19 further comprising a plurality of electrodes mounted on the distal section of the catheter.

21. The apparatus of claim 17, further comprising:
   a source of ablation energy;
   an ablation section on the distal section of the catheter, the ablation section including at least one electrode coupled to the source of ablation energy, and a fluid port for delivering conductive fluid into contact with at least one of the electrodes and to cause said fluid to create a conductive path between said at least one of the electrodes and the tissue when said at least one of the electrodes is positioned adjacent body tissue.

22. The apparatus of claim 21 wherein the ablation section further includes a fluid permeable deformable member at least partially covering said at least one of the electrodes.

23. The apparatus of claim 22 wherein the deformable member includes a layer of foam material formed over said at least one of the electrodes.

24. The apparatus of claim 22, further comprising a covering on the deformable member, the covering formed of a material substantially impermeable to fluid, the covering including at least one opening sized to allow passage of fluid out of the covering.

25. The apparatus of claim 18 wherein the electrodes include electrodes configured to measure electrical activity of adjacent body tissue.

26. A method of positioning a catheter within a body cavity comprising the steps of:
   (a) providing a core wire including a distal portion having a predetermined non-linear shape and further providing a catheter having a pull wire and a lumen proportioned to slidably receive the core wire, wherein the catheter includes a proximal section and a distal section;
   (b) passing the catheter through a vessel and into a body cavity;
   (c) inserting the distal portion of the core wire into the lumen;
   (d) passing at least a portion of the distal portion of the core wire into the distal section of the catheter, causing the portion of the distal portion of the core wire to deform the distal section of the catheter to approximate the non-linear shape of the portion of the distal portion that is within the distal section of the catheter; and
   (e) increasing tension on the pull wire to deflect the distal section of the catheter.

27. The method of claim 26 wherein the catheter further includes at least one electrode on the distal section and wherein the method includes the steps of positioning the distal section adjacent to tissue to be treated and ablating tissue using the electrode.

28. The method of claim 26 wherein the catheter further includes at least one electrode on the distal section and wherein the method includes the steps of positioning the distal section adjacent to tissue to be treated and measuring electrical activity of the tissue using the electrode.

29. A method of positioning a catheter within a body cavity comprising the steps of:
   (a) providing a core wire including a distal portion having a predetermined non-linear shape and further providing a catheter having a pull wire and a lumen proportioned to slidably receive the core wire, wherein the catheter includes a proximal section and a distal section, the distal section having greater flexibility than the proximal section;
   (b) passing the catheter through a vessel and into a body cavity;
   (c) inserting the distal portion of the core wire into the lumen;
   (d) passing the distal portion of the core wire through the proximal section of the catheter, causing the distal portion of the core wire to substantially straighten;
   (e) passing at least a portion of the distal portion of the core wire into the distal section of the catheter, causing the portion of the distal portion of the core wire to deform the distal section of the catheter to approximate the non-linear shape of the portion of the distal portion that is within the distal section of the catheter; and
   (f) increasing tension on the pull wire to deflect the distal section of the catheter.

30. The method of claim 29 further comprising the steps of:
   (f) withdrawing the core wire from the catheter distal section into the catheter proximal section, causing the core wire to substantially straighten;
   (g) withdrawing the core wire from the lumen; and
   (h) after step (g), withdrawing the catheter from the body cavity.

31. The method of claim 29 further comprising the steps of:
   (f) removing the core wire from the catheter;
   (g) providing a second core wire, the second core wire including a second distal portion having a second predetermined non-linear shape;
   (g) inserting the second distal portion of the second core wire into the lumen;
   (h) passing the second distal portion through the proximal section of the catheter, causing the second core wire to substantially straighten; and
   (i) passing at least a portion of the second distal portion of the second core wire into the distal section of the catheter, causing the distal section of the catheter to deform to approximate the non-linear shape of the portion of the second distal portion that is within the distal section of the catheter.

32. The method of claim 29 wherein step (a) includes the step of providing electrodes on the distal section of the catheter and wherein the method further comprises the steps of:

positioning the electrodes into contact with tissue in the body cavity; and delivering RF energy to the electrodes to ablate the tissue.

33. The method of claim 29 wherein step (a) includes the step of providing electrodes on the distal section of the catheter and wherein the method further comprises the steps of:

positioning the electrodes into contact with tissue in the body cavity; and using the electrodes to detect electrical activity of the tissue.

34. The method of claim 29 wherein:

step (a) includes the step of further providing a guiding core wire having a distal portion; and step (b) includes the step of inserting the distal portion of the guiding core wire into the lumen and, after passing the catheter into the body cavity, withdrawing the guiding core wire from the lumen.

35. The method of claim 29 further comprising the steps of positioning the catheter in a desired location within the body and using it to gather diagnostic information and/or to deliver therapy to adjacent tissue.

* * * * *